(12) United States Patent
Dawson

(10) Patent No.: US 8,062,533 B2
(45) Date of Patent: Nov. 22, 2011

(54) DEVICES AND METHODS FOR THE PURIFICATION, ISOLATION, DESALTING OR BUFFER/SOLVENT EXCHANGE OF SUBSTANCES

(75) Inventor: Elliott P. Dawson, Murfreesboro, TN (US)

(73) Assignee: BioVentures, Inc., Murfreesboro, TN (US)

( * ) Notice: Subject to any disclaimer, the term of this patent is extended or adjusted under 35 U.S.C. 154(b) by 0 days.

(21) Appl. No.: 12/674,893

(22) PCT Filed: Jul. 31, 2009

(86) PCT No.: PCT/US2009/052517
§ 371 (c)(1),
(2), (4) Date: Feb. 23, 2010

(87) PCT Pub. No.: WO2010/014970
PCT Pub. Date: Feb. 4, 2010

(65) Prior Publication Data
US 2010/0216220 A1 Aug. 26, 2010

Related U.S. Application Data

(60) Provisional application No. 61/085,591, filed on Aug. 1, 2008.

(51) Int. Cl.
B01L 3/02 (2006.01)
B01D 21/26 (2006.01)
B01D 61/00 (2006.01)

(52) U.S. Cl. ... 210/787; 210/650; 210/101; 210/321.64; 210/321.78; 210/321.87; 210/418; 210/502.1; 210/504; 210/506; 210/500.3; 210/198.2; 210/656; 210/657; 422/513; 422/524; 422/533; 422/534

(58) Field of Classification Search ............ 422/101, 422/513, 514, 527, 524, 533, 534; 210/787, 210/800, 767, 781, 650, 651, 652, 653, 654, 210/655, 198.2, 656, 657, 100, 101, 500.27, 210/500.29, 500.3, 502.1, 504, 506, 321.64, 210/621.72, 321.78, 321.79, 321.87, 360.1, 210/418, 455
See application file for complete search history.

(56) References Cited

U.S. PATENT DOCUMENTS 2,062,539 A 12/1936 Vogt
3,347,247 A * 10/1967 Lloyd .......................... 131/342
3,805,800 A 4/1974 Summers
(Continued)

FOREIGN PATENT DOCUMENTS

JP 2007240525 A * 9/2007

OTHER PUBLICATIONS

International Search Report and Written Opinion for PCT Application No. PCT/US09/52517, dated Oct. 6, 2009, 11 pages.

Primary Examiner — Tony G Soohoo
Assistant Examiner — David C Mellon
(74) Attorney, Agent, or Firm — David A. Farah; Sheldon Mak & Anderson pC

(57) ABSTRACT

A spin column device, which contains a rigid porous filter that retains its shape during centrifugation, chromatography methods using the device to isolate a desired substance, e.g., a biological molecule, from other substances in a mixture, and kits containing the device with one or more reagents for use in the method.

23 Claims, 6 Drawing Sheets

U.S. PATENT DOCUMENTS

| | | | | |
|---|---|---|---|---|
| 4,018,678 A | * | 4/1977 | Peniston et al. | 210/679 |
| 4,174,719 A | | 11/1979 | Martin et al. | |
| 4,270,921 A | * | 6/1981 | Graas | 436/67 |
| 4,282,889 A | | 8/1981 | Dahlgrun | |
| 4,369,117 A | | 1/1983 | White | |
| 5,057,426 A | * | 10/1991 | Henco et al. | 435/270 |
| 5,187,083 A | * | 2/1993 | Mullis | 435/91.1 |
| 5,419,874 A | * | 5/1995 | Coassin et al. | 422/134 |
| 5,648,271 A | * | 7/1997 | Kempe | 436/178 |
| 5,660,984 A | * | 8/1997 | Davis et al. | 435/6.16 |
| 5,876,918 A | * | 3/1999 | Wainwright et al. | 435/4 |
| 5,906,947 A | * | 5/1999 | Bienhaus et al. | 436/518 |
| 6,020,186 A | * | 2/2000 | Henco et al. | 435/287.2 |
| 6,103,195 A | | 8/2000 | Shukla et al. | |
| 6,183,692 B1 | * | 2/2001 | Trese et al. | 422/430 |
| 6,207,601 B1 | * | 3/2001 | Maurer et al. | 442/333 |
| 6,221,655 B1 | * | 4/2001 | Fung et al. | 435/288.1 |
| 6,401,552 B1 | | 6/2002 | Elkins | |
| 6,761,855 B1 | * | 7/2004 | Cook et al. | 422/70 |
| 7,291,263 B2 | * | 11/2007 | Ward et al. | 210/198.2 |
| 2003/0069413 A1 | * | 4/2003 | Pai et al. | 536/25.4 |
| 2005/0191760 A1 | * | 9/2005 | Heath et al. | 436/177 |
| 2006/0037903 A1 | | 2/2006 | Smith et al. | |
| 2006/0118491 A1 | | 6/2006 | Gjerde et al. | 210/656 |

* cited by examiner

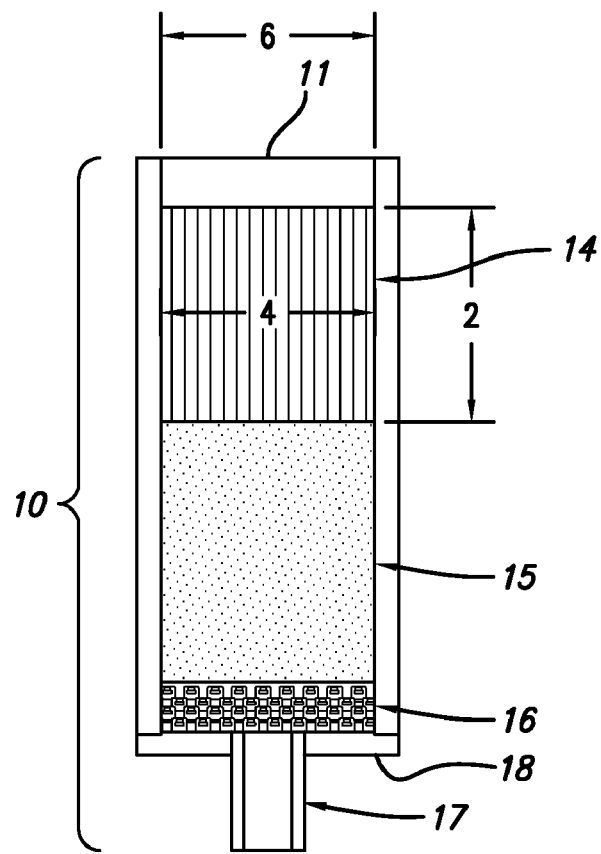
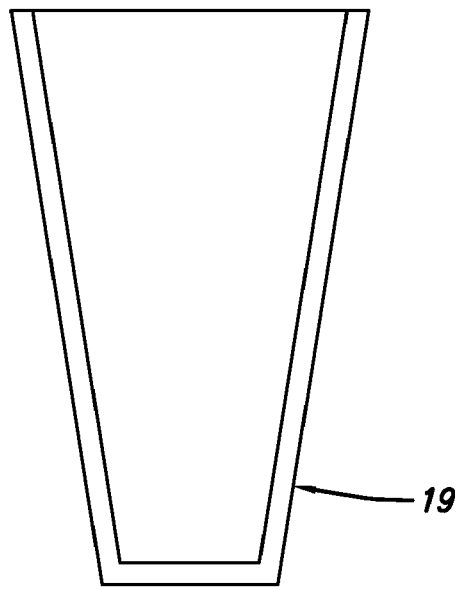
FIG. 1

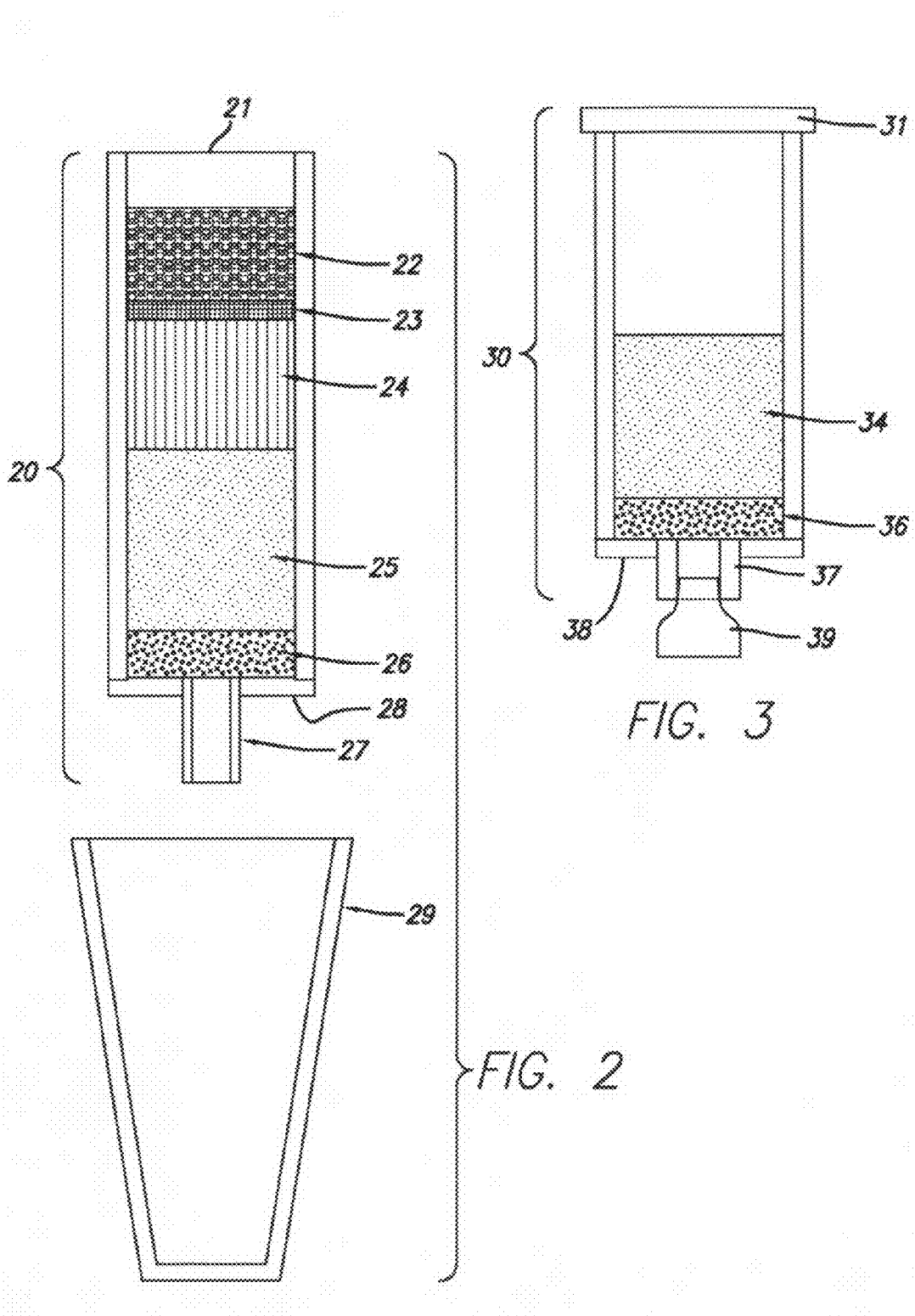

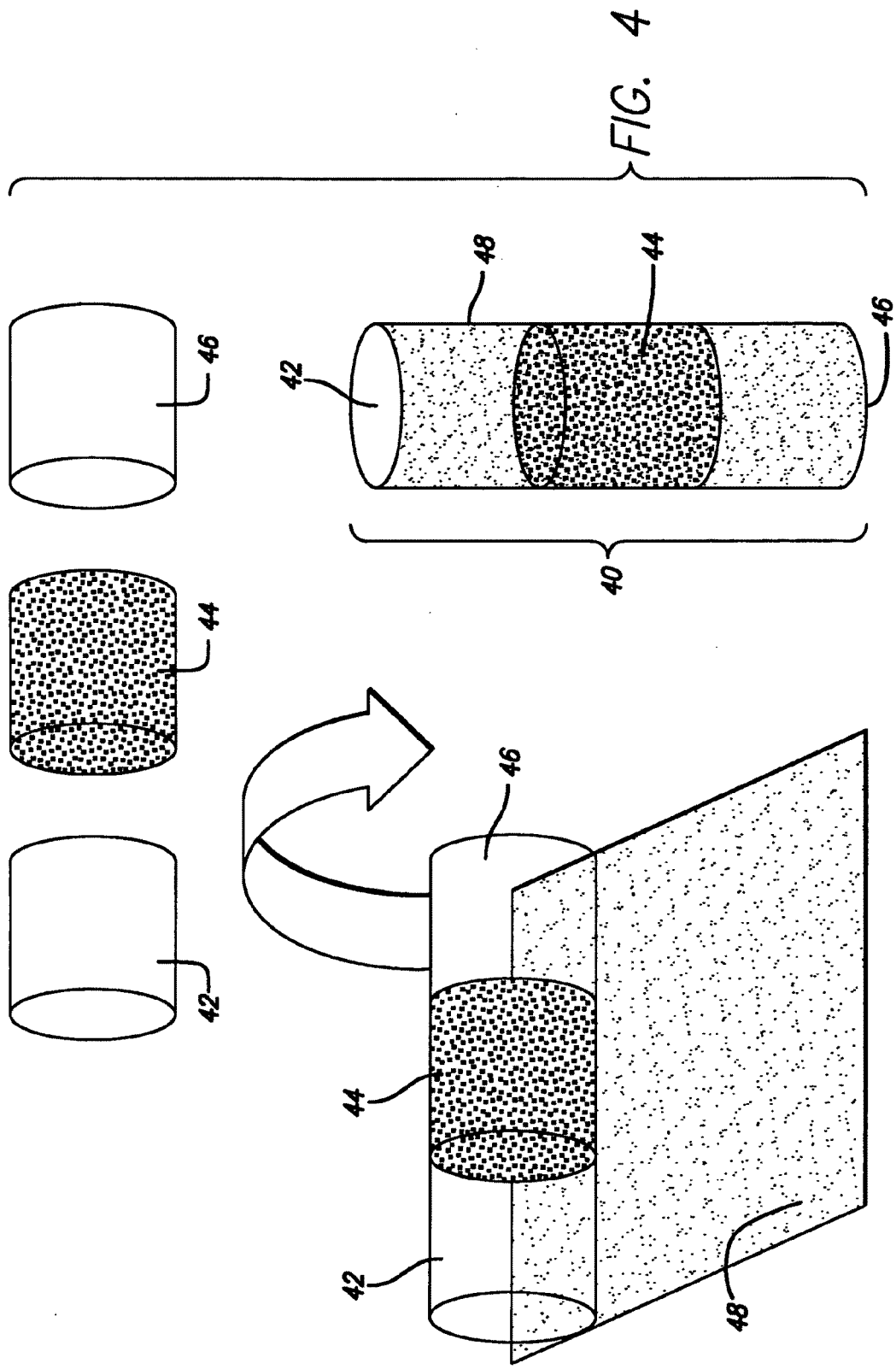

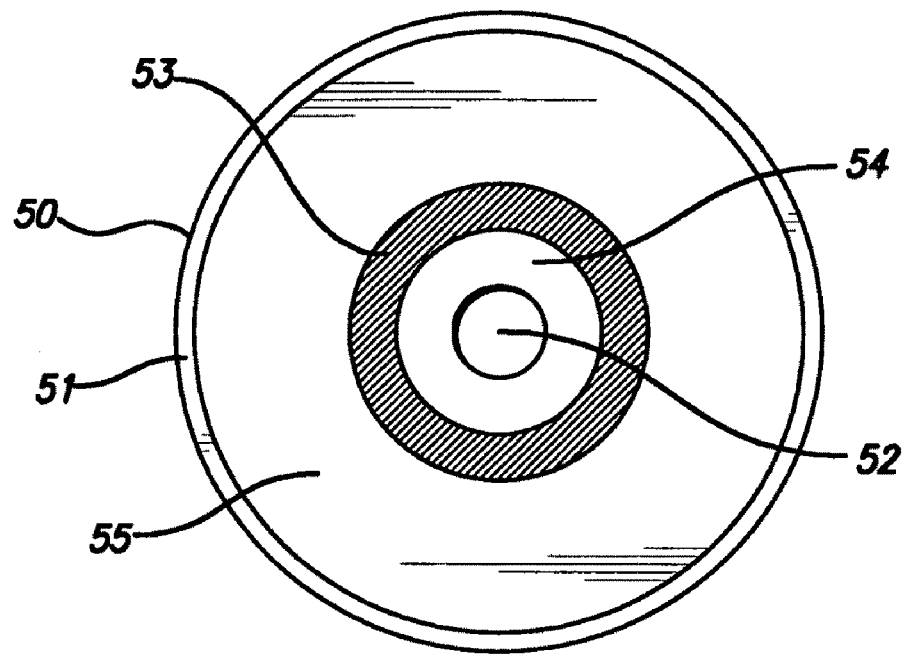
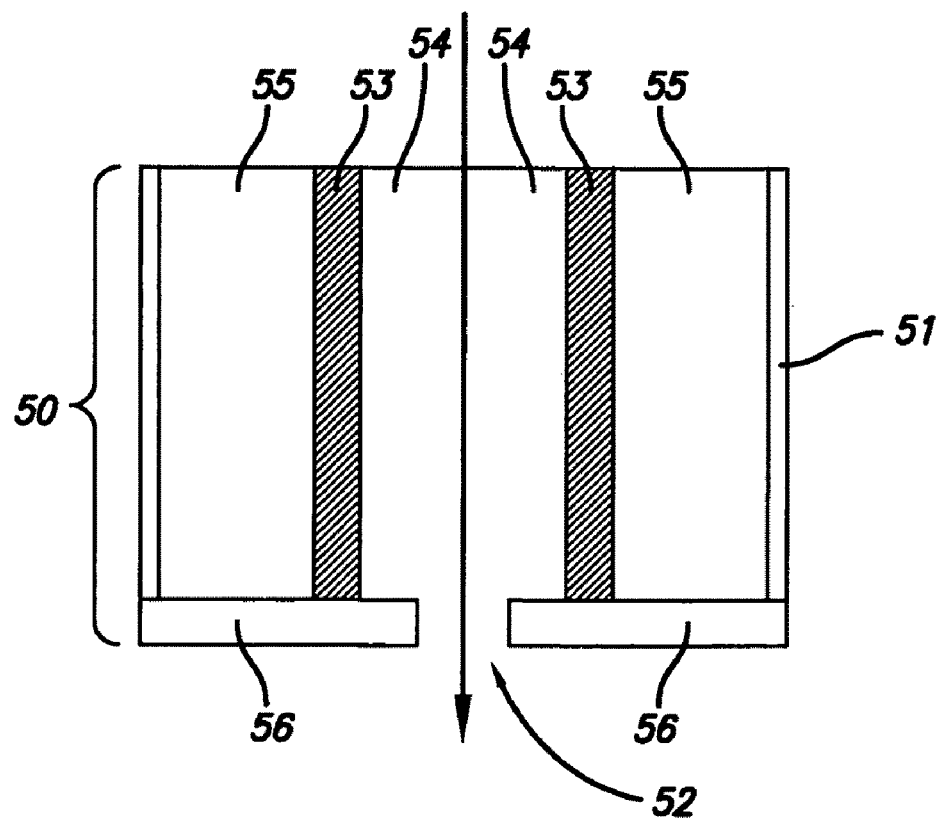
FIG. 5

DEVICES AND METHODS FOR THE PURIFICATION, ISOLATION, DESALTING OR BUFFER/SOLVENT EXCHANGE OF SUBSTANCES

CROSS REFERENCE TO RELATED APPLICATIONS

This application is the U.S. national stage of International Application No. PCT/US09/52517 filed Jul. 31, 2009 and entitled "Devices And Methods for the Purification, Isolation, Desalting or Buffer/Solvent Exchange of Substances," which claims the benefit of U.S. Provisional Patent Application No. 61/085,591, filed Aug. 1, 2008, the disclosure of which is incorporated by reference in its entirety.

BACKGROUND

Frequently in chemical, biological or materials assay procedures it is necessary to isolate or purify a desired substance/s from other substance/s. Column chromatography of various types are commonly used for such procedures. In particular, a simple form of chromatography, namely spin-column chromatography is frequently employed to enrich for analytes, to reduce or remove interferences or combinations of these purposes. Such spin-columns are of simple design and usually contain a separation media such as cross-linked dextrans or polyacrylamides, ion-exchange resins or silica gels of various types.

Generally, the spin-column devices are prepared by having the separation media suspended in a buffer or organic solvent within the spin-column. Before centrifugation the separation media has an essentially uniform distribution in the spin column and when viewed perpendicular to its surface has a circular cross section. Usually, the spin-column is pre-spun in a centrifuge, preferably equipped with a "swinging-bucket" rotor to keep the bulk mass of the separation media within the column from slanting and to maintain a uniform flow path for the suspension media and sample material that is parallel to the walls of the column. Following centrifugation in a "swinging bucket" rotor the separation media has an essentially uniform distribution in the spin column and when viewed perpendicular to its surface has a circular cross section. A fixed angle rotor is sometimes used, but the column media shifts and forms an angled surface. Following centrifugation in a "fixed angle" rotor the separation media has an uneven distribution in the spin column and when viewed perpendicular to its surface has an elliptical or ovoid cross section. Applied samples then flow at an angle through the separation media and not parallel to the column walls.

Regardless of the type of rotor used, the applied sample must preferably be loaded to the center of the media. Frequently, the spin-column is pre-spun to force the liquid suspending the separation media through the column to remove excess liquid from the spin-column and compact the separation media. The sample is then carefully loaded onto the top center of the separation media in the spin-column and the spin-column is centrifuged in a collection tube and the desired material is collected in the collection tube. When spin-columns have been pre-spun, care must be taken that the spin-column is in the identical orientation as it was during the pre-spin, otherwise the media and applied sample will be redistributed during centrifugation and the desired separation/filtration will be inadequate or compromised.

In some cases, the desired material is retained on the separation media within the spin-column and is subsequently eluted, sometimes after washes to remove undesired materials, with the desired material being displaced from the separation media within the spin-column by some alteration of conditions facilitating its release from the column separation media, and sometimes the desired material is not bound and interferences are bound to the separation media.

There are many examples of the use of spin-columns, for example to accomplish buffer exchange of proteins, such as antibodies, or to separate unincorporated radioactive nucleotides from polynucleotides which have incorporated the radiolabel, for example, following radioactive phosphorylation of DNA for use as probes from γ-32P-ATP. There are many other examples well known in the art and described in many manuals or web sites describing molecular biology, labeling or purification protocols or other techniques. See for example, CSH Protocols at Cold Spring Harbor Protocols Online or the Wikipedia location on the world wide web, entitled "Spin column-based nucleic acid purification," for a description of minicolumn DNA preparation.

Other useful guides are: *Protein analysis and purification: benchtop techniques*, by Ian M Rosenberg, Birkhäuser, Boston® 2005, 2nd ed pp 337-339, which describes use of spin columns to accomplish buffer exchange; *Affinity Chromatography: Methods and Protocols*, by Michael Zachariou, Springer, N.Y., 2007, pp. 156-157, which describes affinity purification from cell lysates using spin columns by centrifuge and by vacuum; Hoyt P R, Doktycz M J, Warmack R J, Allison D P., Spin-column isolation of DNA-protein interactions from complex protein mixtures for AFM imaging, *Ultramicroscopy*. 2001 January; 86(1-2):139-43; and Nickoloff J A, Sepharose spin column chromatography. A fast, nontoxic replacement for phenol:chloroform extraction/ethanol precipitation. *Mol Biotechnol*. 1994 February;1(1):105-8.

Often, to obtain proper separation, the spin-column devices must be centrifuged in a swinging bucket type of rotor to keep the media from slanting and distorting the separation process. When spun in a fixed angle rotor the separation media becomes distorted or becomes slanted and the applied sample material and liquids experience various separation path lengths or channeling through the column, with the sample material in the lower aspect of the slanted media experiencing a short separation path and the sample material at the high end of the slope experiencing longer separation paths. This behavior of the applied sample material is in conflict with good separation performance. Ideally, as is well known in chromatography theory and practice, the separation media should have similar effective separation paths across the diameter of the separation media and along the length or depth of the separation media; however, channeling or significant distortions of the separation path greatly compromises and significantly alters and adversely affects the performance of the separation process. There is therefore a need for more convenient, efficient and effective spin column devices that overcome the problems of channeling, special centrifuge rotors, centered sample loading, and single purpose utility of present spin column devices.

SUMMARY

According to one embodiment of the invention, there is provided a spin column assembly, comprising: spin column device, the spin column device comprising; 1) a column, the column having an inner diameter and an upper opening, and 2) a lower end, the lower end containing an effluent port, where the effluent port comprises an opening small enough to retain or impede the exit of solid or particulate matter from the spin column device, but large enough to allow passage of effluent liquids; separation media contained within the spin column device, the separation media having an upper surface; and a rigid porous filter placed within the spin column device above the separation media and in close contact with the upper surface of the column separation media, the porous filter having diameter about equal to the inner diameter of the spin-column and a height greater than half the inner column diameter.

In one embodiment the height of the rigid porous filter is about equal to the inner column diameter. In a preferred embodiment the rigid porous filter is inflexible enough to maintain its shape during centrifugation.

In one embodiment of the spin filter assembly the rigid porous filter comprises a fiber selected from the group consisting of cellulose, cellulose acetate, nitrocellulose, polyethylene, nylon and TEFLON®. In another embodiment of the spin filter assembly the rigid porous filter comprises a sintered material selected from the group consisting of plastic, ceramic and metal.

In one embodiment of the spin filter assembly the separation media is selected from the group consisting of: cross-linked dextrans, polyacrylamides, cellulose particles, ion exchange resins, silica particles, silica gels, and affinity chromatography media.

In one embodiment of the spin filter assembly the spin column device is comprised of plastic, glass or treated paper.

In one embodiment of the spin filter assembly the effluent port comprises a screen.

In one embodiment of the spin filter assembly includes a media support seated above the lower end and below the separation media. In a preferred embodiment the media support is a polyethylene frit, filter paper or membrane.

In one embodiment, the spin filter assembly further comprises a collection vessel for collecting the column effluent.

One embodiment of the spin filter assembly includes a grinding or pulverizing agent, such as beads made of ceramics, glass or metal or combinations of such beads. In a preferred embodiment, a grinding or pulverizing agent is placed above the rigid porous filter. In another embodiment a protective frit is placed between the grinding or pulverizing agent and the rigid porous filter.

One embodiment of the spin filter assembly includes a cap covering the upper opening of the spin column device.

One embodiment of the spin filter assembly includes a closure plugging the effluent port.

One embodiment of the spin filter assembly includes a volume control device placed within the upper opening of the spin control device and above the rigid porous filter, the volume control device comprising: a) an outer column; b) a base attached below the outer column, the base containing a hole, where the hole in the base impedes or prevents the flow of fluid due to surface tension effects under normal gravity, but permits the flow of fluid through the hole under higher gravitational or other forces; c) a hollow inner cylinder attached to the base and situated within the outer cylindrical column, the inner cylinder having a height and inner diameter; d) a first cavity within the hollow inner cylinder and above the base having a fixed volume, where the height and inner diameter of the inner cylinder determines the fixed volume; and e) a second cavity outside the inner cylinder, but within the outer column and above the base.

In one embodiment of the spin column assembly the volume control device is composed of rigid, inert material impermeable to liquids, such as metal, glass, plastic or paper impregnated with polymer. In a preferred embodiment the volume control device is constructed of plastic by injection molding.

One simple version of the spin column assembly comprises: a) a spin column device, the spin column device comprising; 1) a column, the column having an inner diameter and an upper opening; and 2) a lower end attached to the column, the lower end containing an effluent port, where the effluent port comprises an opening to allow passage of effluent liquids; and b) a rigid porous filter placed within the spin column device above the lower end of the spin column device, the porous filter having diameter about equal to the inner diameter of the spin-column and a height greater than half the inner column diameter, where the rigid porous filter is comprised of cellulose or cellulose acetate fibers imbedded with charcoal, ion exchange particles or combinations thereof.

One embodiment of the present invention provides a monolithic HGR filter assembly, comprising a plurality of cylindrical elements, each cylindrical element having a curved outer surface, the cylindrical elements comprising; 1) a first filter element and 2) a separation media element, where the plurality of cylindrical elements are aligned next to each other and held together by a casing, the casing coating the curved outer surfaces of the cylindrical elements. Preferably, the casing is made of a material impermeable or only slightly impermeable to liquid, such as cellophane or polyvinyl chloride film. In preferred embodiments of the monolithic HGR filter assembly, the first filter element comprises fiber or sintered filter material and the separation media element comprises separation media or fiber impregnated with or coated with separation media. In one embodiment of the monolithic HGR filter assembly the plurality of cylindrical elements further comprises a second filter element, wherein the separation media element is situated next to and between the first and second filter elements. Preferably, the second filter element comprises fiber or sintered filter material.

Another embodiment provides a spin column assembly, comprising: a) a spin column device having an inner diameter and an inner radius; and b) the monolithic HGR filter assembly inserted within the spin column device, the filter assembly having a diameter about equal to the inner diameter of the spin-column device and of a height greater than the inner radius of the spin-column device.

One embodiment of the present invention entails a method of separating a desired substance from other substances in a sample, including the steps of: a) providing a sample comprising a solution or suspension containing the desired substance; b) loading the sample onto the spin column assembly that contains an HGR-filter; c) placing the spin column assembly in a suitable collection vessel; d) applying sufficient force to the spin column assembly and collection vessel to drive fluids in the sample through the effluent port into the collection vessel; e) eluting the desired substance from the spin column assembly; and f) collecting the eluted substance in the collection vessel. In a preferred embodiment the desired substance is a biological molecule of interest, such as DNA, RNA, protein or glycoprotein. In another embodiment, the sample comprises disrupted cells or tissues suspended in lysis buffer. In some embodiments, sufficient force is applied to the spin column assembly and collection vessel by gravitation, pressure, vacuum or centrifugation. In a preferred embodiment, sufficient force is applied to the spin column assembly and collection vessel by centrifugation in a fixed angle rotor.

Another embodiment of the present invention entails a method of separating a biological molecule of interest from other substances in a sample, which includes the steps of: a) providing a sample comprising a solution or suspension containing the biological molecule of interest; b) obtaining a spin column assembly that includes a grinding or pulverizing agent; c) mixing the sample with the grinding or pulverizing agent in the spin column assembly; d) placing the spin column assembly in a suitable collection vessel; e) applying sufficient force to the spin column assembly and collection vessel to drive fluids in the sample through the effluent port into the collection vessel; e) eluting the biomolecule of interest from the spin column assembly; and f) collecting the eluted biomolecule of interest in the collection vessel. In one embodiment of the method, the mixing step includes mechanical agitation of the spin column assembly before or after placing the spin column assembly in a suitable collection vessel.

One embodiment provides a kit, which can include a) a spin column assembly; and b) at least one or more than one reagent for use in an isolation or purification procedure selected from the group consisting of lysis buffer, wash buffer, elution buffer and stock solutions for preparing such buffers.

Another embodiment provides a kit comprising: a) one or more than one spin column device having an inner diameter and an inner radius; and b) one or more than one monolithic HGR filter assembly, the filter assembly having a diameter about equal to the inner diameter of the spin-column device and of a height greater than the inner radius of the spin-column device.

FIGURES

These and other features, aspects and advantages of the present invention will become better understood with regard to the following description, appended claims, and accompanying figures where:

FIG. 1 illustrates an embodiment of the spin filter assembly;

FIG. 2 illustrates an embodiment of the spin filter assembly, which contains pulverizing or grinding agents;

FIG. 3 illustrates of another simple embodiment of the spin filter assembly;

FIG. 4 depicts of assembly of cylindrical filter and separation media components to produce a monolithic HGR filter assembly;

Figure 6:
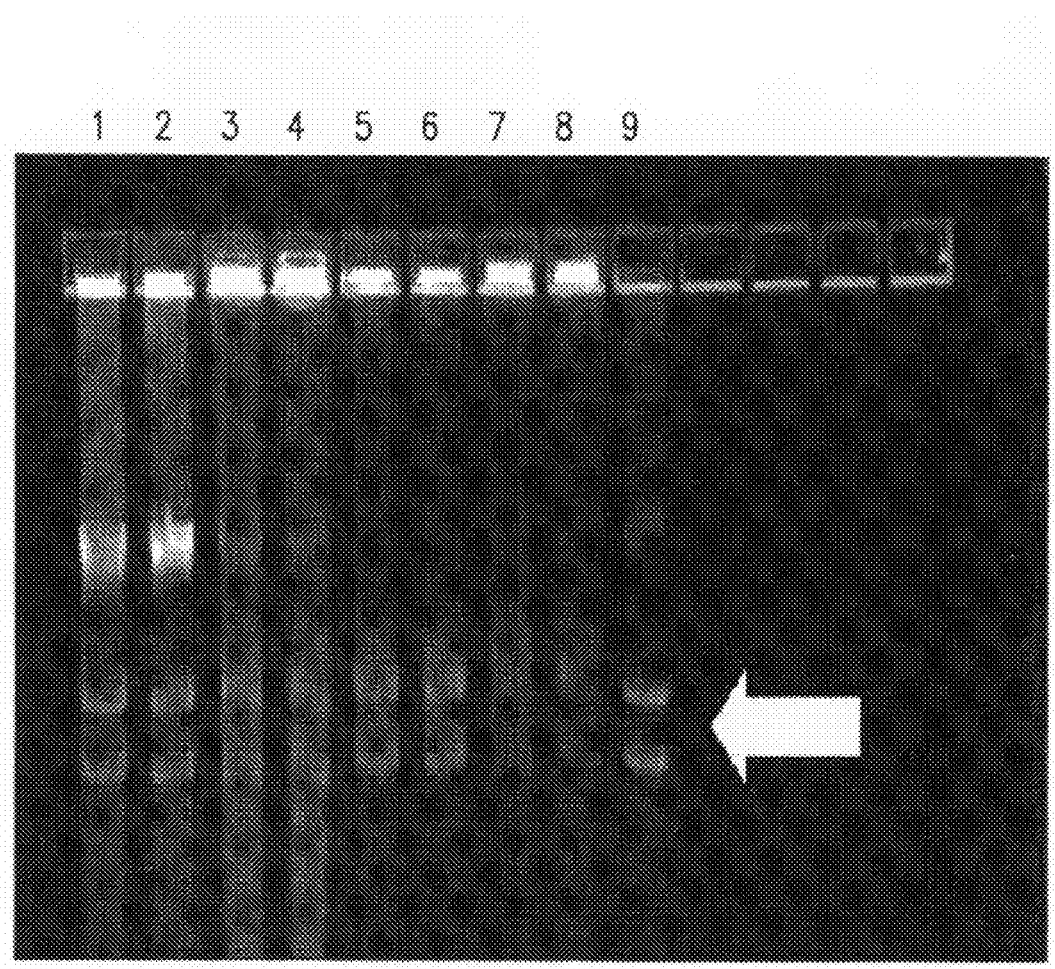
Figure 7:
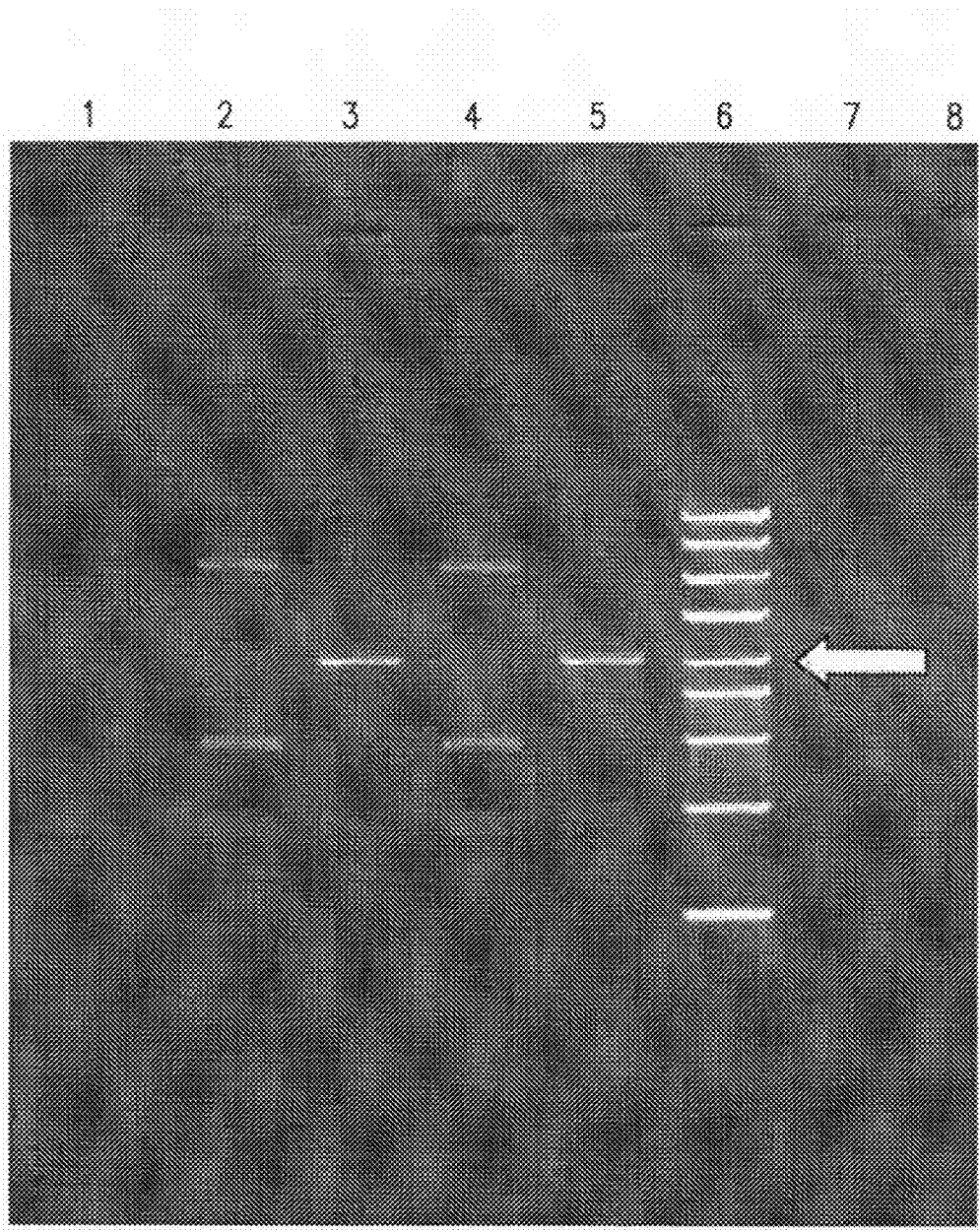

FIG. 5. shows a device for regulating the volume of fluid delivered to the surface of the spin column assembly;

FIG. 6. shows a gel electrophoretic indication of the presence of ribosomal RNA isolated using the spin filter assembly; and FIG. 7 shows a gel electrophoretic indication of plasmid DNA isolation and suitability of the isolate for Bam HI digestion.

DESCRIPTION

As used in this disclosure, except where the context requires otherwise, the term "comprise" and variations of the term, such as "comprising," "comprises" and "comprised" are not intended to exclude other additives, components, integers or steps.

The inventor has found that using a rigid porous filter or frit referred to herein as an HGR-filter (where HGR represents Height Greater than or equal to the Radius), placed above the spin column separation or packing media and in close contact with the upper surface of the spin column separation media, enables a spin-column to be used in either rotors of a swinging bucket type or fixed angle type without the generation of slanted or other distortions of the separation media. Such a filter should be of a diameter equal to the inner diameter of the spin-column and of a height greater than half the inner column diameter or greater than the inner radius of the spin-column. Additionally, the HGR-filter affords a flow of liquids through the separation media more parallel to the centrifugal forces than spin-columns without this HGR-filter or those with frits of shorter heights.

Further, the inventor has found that such devices can be configured to accomplish sample disruption in the region above the HGR-filter set forth above, which for example can facilitate the isolation of polynucleotides or proteins from cells or tissues saving significant sample preparation time and expense and substantially reducing complicated manipulations, for example, in the preparation of samples for clinical, investigational research, quality control or other forms of analysis.

In addition, the means of eluting the sample from the column may employ gravitation, pressure or application of vacuum in addition to centrifugation to capture, wash, elute or otherwise recover the desired sample material, from the HGR-devices disclosed herein, thereby providing a device of wider utility than either other spin-column devices or traditional columnar devices alone.

Importantly, the inventor has found other useful configurations for the HGR-devices as described in more detail in the following disclosure.

FIG. 1 shows one embodiment of the present invention, referred to herein as a spin-column assembly. Spin-column assemblies constructed in accordance with this embodiment are comprised of several components, including: a device referred to as a spin-column device 10, comprising a column made of plastic, glass or treated papers, having an upper opening 11 and a lower end 18, the lower end having an effluent port 17, which retains or impedes the exit of solid or particulate matter, but allows the passage of effluent liquids. Typically the device contains a media support 16, such as a frit, seated above the bottom end of the device to further prevent loss of separation media from the spin column device 10. The device also contains separation media 15 within the column loaded above the media support. A rigid porous filter 14, having a filter height 2 equal to or greater than the inner radius of the selected spin-column device and a filter diameter 4 that is preferably only slightly smaller than the inner diameter 6 of the spin-column device, i.e., the HGR-filter, is inserted within the spin column device, above the packing or filtration media 15. Optionally, the assembly can also include a cap for enclosing the upper opening and a closure for the effluent port 17 to prevent entry of contaminants or loss of materials from the spin-column device. The spin-column device is usually of a diameter sufficient to fit within a collection vessel 19, such as a 1.5-2 ml microfuge tube or 15-50 ml conical centrifuge tube, which acts as a collection vessel 19 in which to collect the effluent from the spin-column. The assembly of these components with an HGR-filter is referred to as an HGR spin-column assembly or as an HGR-device. It should also be noted, as will be described below, that the HGR-filter can function individually as a frit, filter or separation media or have functional combinations of these or other functionalities in either a single HGR-filter as combinations of HGR-filters. HGR-devices are configurable as single sample devices or as multi-well HGR-devices to process multiple samples in parallel.

FIG. 2 shows a preferred embodiment of the present invention, which can be used to release material from a sample, such as to lyse a cell to release its constituents. In addition to the spin column device 20, having an upper opening 21, a lower end 28 and an effluent port 27, the spin column device contains, bottom to top, a media support 26, separation or packing media 25 and an HGR-filter 24. The spin-column device 20 is usually of a diameter sufficient to fit within a collection vessel 29, such as a 1.5-2 ml microfuge tube or 15-50 ml conical centrifuge tube, which acts as a collection vessel 29 in which to collect the effluent from the spin-column. In addition, the region above the HGR-filter contains a grinding or pulverizing agent 22, like beads, such as those made of ceramics, glass or metals or combinations of such beads. In embodiments where sample disruption is to be effected, it is desirable to protect the upper surface of the HGR-filter 24 to prevent its erosion by the action of the grinding/pulverizing agents 22. In such a case, the upper portion of the HGR-filter 24 is covered by a thin protective frit 23 or other porous material resistant to the action of the pulverizing agent 22 employed to accomplish lysis and/or mechanical disruption of the sample. Suitable beads are well known in the art and may be selected from micron to millimeter sized borosilicate glass, soda lime glass, ceramics particles such as zirconia, silica, alumina and the like, or metal balls such as stainless steels of various alloy composition and tinsel strengths. The beads being in the size range of microns to millimeter in average size depending on the nature composition and sample composition sought to be disrupted. For example 0.5 mm zirconia/silica particles are suitable for most cells and most soft tissues while 1-5 mm stainless steel beads are more suitable for tougher materials like plant tissues, such as corn, wheat, soybeans and the like such selection being known in the art.

FIG. 3 shows an alternative embodiment of the spin column assembly, where the spin column device 30, which has a lower end 38 and an effluent port 37, simply contains a media support 36, such as a frit, seated above the bottom end of the device and a rigid porous filter 34, i.e., the HGR-filter, sitting on top of the media support 36. This version of the spin column assembly also includes a cap 31 covering the top of the device and a closure 39 for plugging up and preventing leakage from the effluent port 37.

FIG. 4 shows one embodiment of the present invention, referred to herein as a monolithic HGR filter assembly, which can be inserted in another device, such as a spin column device as described herein. The monolithic HGR filter assembly 40 includes a plurality of cylindrical elements, e.g., a first filter element 42, a second filter element 46, and separation media element 44 situated between the first and second filter elements, which are held together and coaled, such as by rolling as depicted in FIG. 4, with a thin surface element such as cellophane or polyvinyl chloride film to provide a casing 48. The casing 48 serves to hold the assembly together and is impermeable or only slightly impermeable to the liquid media contained in the sample to be captured by the separation media. In preferred embodiments the first and second filter elements 42, 46, are comprised of fiber or sintered filter material and the separation media element 44 is comprised of separation media or fiber impregnated with or coated with separation media, such as cross-linked dextrans, cellulose particles, ion exchange resins, silica particles or gels of various types or affinity chromatography media.

FIG. 5 shows a top view of a volume control device 50 for regulating the volume of fluid delivered to the upper surface and center of a spin column assembly. The volume control device can be placed within the upper opening of a spin column device on top of the rigid porous filter. The volume control device 50 is comprised of a larger outer column 51 and base 56 with a small hole or opening 52 in the base 56 that under normal gravity impedes or prevents the flow of fluid due to surface tension effects but under higher gravitational loading or other forces permits the flow of fluid through the opening 52. Attached to the base 56 and situated within this outer cylindrical column 51 is an inner hollow cylinder 53 whose height and inner diameter determine a fixed volume of fluid. If an excess of fluid is delivered to a first cavity 54, defined within the hollow inner cylinder 53 and base 56, it will overflow and be retained in a second cavity 55, defined by the inner cylinder 53 walls, the outer column 51 and the base 56, without being delivered to the upper surface of the spin column assembly and only the fluid in the first cavity 54 will pass through the lower opening 52 onto the receiving spin column assembly. The volume control device is composed of rigid, inert material impermeable to liquids, such as metal, glass, plastic or paper impregnated with polymer. A preferred embodiment of the volume control device 50 is constructed of plastic by injection molding.

Selection of Spin-Column Devices for HGR-Devices:

Typically, spin-column devices are comprised of a column composed of plastic, often polymeric such as polyethylene, polypropylene, polycarbonate, polystyrene, glass and the like. The spin-column device is usually of a diameter sufficient to fit within a collection vessel, such as a 1.5-2 ml microfuge tube or 15-50 mil conical centrifuge tube, which acts as a collection vessel in which to collect the effluent from the spin-column. The diameter of the upper opening is usually of the same diameter over the length of the spin-column; however, the lower end of the spin-column usually has a passage that is substantially smaller than the diameter of the body of the spin-column which acts as an exit or discharge port for the fluid effluent from the spin-column. The lower end of the spin-column acts as a support for a porous frit, filter or other support that will allow effluent fluids to pass through it but has the ability to retain and impede or prevent the passage or exit of the particulate or gel separation media from the spin-column. Some columns have an upper frit, while many do not. Empty spin-column devices suitable for use to produce HGR-devices in accordance with the present disclosure are commercially available from a variety of sources such as Thermo-Fisher Scientific (Waltham, Mass,), Sigma Aldrich (Saint Louis, Mo.), Axygen Biosciences (Union City, Calif.), BioRad (Hercules, Calif.), Pierce Chemical Co (Rockford, Ill.), and other suppliers.

The spin-column devices can be selected from a variety of sizes, from about 200 µl to a few tens of milliliters of internal column volume. Preferably, the effluent port of the spin-column device should have a snap off tab or some other end closure to prevent the inadvertent loss of liquids or materials from the effluent port at its base and should also have a cap or other closure for the upper aspect of the device to likewise prevent loss of materials from the column. Such tabs or closures also minimize inadvertent or other contamination of the devices. The lower part of the spin-column device may have a frit or other porous or semi-permeable supporting material, such as a semi-permeable membrane, mesh or filter paper, which acts to retain the separation or filtration media within the assembled spin-column while permitting the flow of liquids through it when the column is subjected to appropriate centrifugation forces, i.e., pressure or vacuum, to move the fluids through and out of the column and into a collection device. For example, one standard frit material is 1.5 mm thick hydrophobic polyethylene with a pore size of 20 µm. In another embodiment the spin-column device is not a single tube as set forth above but is of a multi-well format adapted for use with a 96 well or 384 well plates as collection vessels. Such spin-filter plates are widely available which can accommodate small volumes in each plate well, such as 10 µl up to rather substantial volumes in the tens of milliliters. In this embodiment the wells may be of circular, square, rectangular or of other cross sectional shape. The forgoing selection aspects for spin-column devices also apply to such multi-well formats.

Selection of Separation or Filtration Media for the HGR-Devices:

The separation media can be selected from a variety of materials well known in the art and dependent upon the type of purification to be undertaken by the use of the device. In various embodiments, such media can be comprised of cross-linked dextrans such as the series of SEPHADEX® (GE Health Care; Cardiff, United Kingdom), polyacrylamides such as the BIOGEL® series (BioRad), cellulose particles, ion exchange resins such as AMBERLITES® (Rhom and Haas Chemicals, LLC; Philadelphia, Pa.), DOWEX® (Dow Chemical Company; Midland, Mich.) and others commercially available from a variety of distributors and resellers. In other embodiments, silica particles or gels of various types or affinity chromatography media can be employed as separation or filtration media for the HGR-devices, such media and purposes being well known in the art. The media may be pre-swollen and added to the spin-column devices, or more preferably added dry to the columns and swollen in situ by addition of suitable swelling agent such as for example water for the Sephadex® materials, such procedures being known to those skilled in the art.

Selection of the HGR-Filter for the HGR-Devices:

The HGR-filter of the present disclosure should be porous and yet rigid enough to maintain its shape upon the application of whatever range of pressure, vacuum, centrifugal or gravitational force may be employed during the relevant purification, isolation, desalting or buffer/solvent exchange procedure. Preferably, the rigid porous HGR-filter is sufficiently inflexible to retain its shape upon application of centrifugal force of about 1,000×g to about 12,000×g or more.

Suitable materials for the HGR-filter include fibers, comprised of cellulose, cellulose acetate, nitrocellulose, polyethylene, nylon, TEFLON® and the like. In another embodiment the HGR-filter is comprised of sintered material, such as plastic, ceramic or metals and the like. The HGR-filters may be fabricated such that the fibers are aligned circularly, parallel, perpendicular, spiraled or randomly to the axis of the HGR-filter. In certain embodiments the HGR-filter may be impregnated throughout its dimensions with separation media such as ion-exchange resins or particles, silica particles, affinity separation media such as for example streptavidin coated particles, gel permeation media such as SEPHADEX® and the like. In other embodiments the surface of the HGR-filter material is modified to provide separation functionality by, for example, coating or derivatization to impart such functionality, such as hydrophilic coatings or hydrophobic coatings, or attachment of affinity ligands, such as biotin or streptavidin to the surface of the HGR-filter material. In one embodiment, the HGR-filter can be prepared from cellulose or cellulose acetate filters, usually used as cigarette filters and available under several brand names, such as Rayo, Escort, Joker or other brands offered by Imperial Tobacco and its subsidiaries, such as Robert Burton Associates Ltd. in the United States or other suppliers. Filrona Filtrona (Richmond, Va.) has a broad offering of such filters and includes some with imbedded materials, such as activated charcoal, ion exchange particles and combinations thereof, being marketed as, for example, CAVITEC® filters and the like. The intended use of such filters has been to remove particulates and other undesirable substances from cigarette smoke in order to remove or reduce some of the many undesirable substances such as carcinogens from the smoke. The application of these filters in the present disclosure is a new use and unanticipated, to the best of the inventor's knowledge, by the manufacturer. Additionally, surface activated fiber and plastic materials are also available from Filtrona or its subsidiaries or divisions as well as other vendors. Suitable materials for HGR-filter preparation such as sintered, woven or compressed materials of plastic composition and the like are also available from Filtrona or Porex Technologies (Fairburn, Ga.) and other venders.

The dimensional characteristics of the HGR-filter for the production of HGR-devices are that the height of the HGR-filter is equal to or greater than the radial dimension of the interior dimensions of the selected spin-column device set forth above. Moreover, the diameter of the HGR-filter is only slightly smaller than the inner diameter of the selected spin-column device. The HGR-filters can be prepared such that their dimensions conform to a height greater than or equal to the internal radius of the selected spin-column device and are of a diameter approximately equal to the inner diameter of the spin-column device. In another embodiment, where the HGR-filter is to be used in a multi-well plate such as a 96 well or 384 well plate configuration the dimensional considerations for circular wells is identical to that for columns described above. However, when the cross section of the wells of the multiplate is square, rectangular or hexagonal or the like, then the height of the HGR-filter is preferably equal to or greater than that of the shortest side of the cross sectional dimension of the well and the cross section of the HGR filter essentially matches or closely corresponds to the dimensions and shape to that of the well into which it is to be placed.

In a particularly preferred embodiment, the HGR-filter is sheathed with either an impermeable or permeable coating or layer such as dense paper or plastic or polymeric coating which may be either hydrophobic or hydrophilic regarding its surface properties applied on the outside surface of the HGR-filter generally parallel to the long or vertical axis of the filter with respect to its alignment within the spin-column device. For example, in an embodiment where the HGR-filter is cylindrical, the curved surfaces of the cylindrical HGR-filter are sheathed with an impermeable or permeable coating, whereas the flat surfaces at the top and bottom of the HGR-filter remain free of the coating.

Assembly of Components to Produce and Use the HGR-Device:

Spin-column devices are selected according to the criteria discussed above and according to the volume of sample to be processed and a matching collection device suitable to retain the HGR-device and the expected effluent volume of fluids expected to be collected from the HGR-device to be fabricated. In a preferred embodiment the HGR-filter should have a diameter approximately equal to the inner diameter of the spin-column. This HGR-filter should have a height or long axis of greater than 0.5 times the column inner diameter or equal to or greater than the inner radius of the spin-column device. In one embodiment HGR-filter acts to stabilize the underlying column packing or separation media especially when used in fixed angle centrifuge rotors preventing this media from sloping when spun in such devices. In another embodiment the HGR-filter acts as a pre-filter to remove particulates or other materials which can block the flow through the column packing/separation media. The HGR-filter can be selected from a number of materials such as cellulose fibers, cellulose acetate fibers, plastic fibers, it may be prepared from sintered materials such as plastics, ceramics, glass or metals, in addition it may be of a mesh like material composed of materials set forth above. The HGR-filter may have the fibers in a fixed orientation such as parallel to the long axis, perpendicular to the long axis or as a spiral relative to the long axis or the fibers or material of the filter may be of a random orientation, such selection and configurations being chosen based on the intended use and purpose of the device.

Several broad embodiments of the HGR-devices are possible for example, where the spin-column device has a frit at its base and the space above this is filled with separation media partially filling the device and an HGR-filter is inserted atop the separation media. In another embodiment to prepare an HGR-device, the spin-column has no frit and the HGR-filter is inserted to contact the base aspect of the spin-filter device. In another embodiment of an HGR-device the HGR-filter is inserted into the spin-column which may or may not have a frit at its base and separation media is added above the HGR-filter and another HGR-filter is inserted atop the separation media forming a sandwich of separation media between two HGR-filters. Numerous other embodiments of HGR-devices varying with the order of assembly of HGR-filters and separation or lysing media within the spin-column device can readily be envisioned from the teachings of this disclosure by those skilled in the art.

Methods of Use

Use of a spin column assembly containing a rigid porous HGR filter provides many advantages in chromatographic procedures used to isolate or purify a desired substance from other substances, particularly when the desired substance is a biological molecule, such as DNA, RNA, protein or glycoprotein, contained within cells or tissues. The rigidity of and the dimensions of the filter permits centrifugation procedures using fixed angle rotors. Moreover, the ability of the filter to act as a pre-screen, trapping particulate matter, permits sample preparation and subsequent chromatography steps to be performed in a single device, obviating the need for additional pre-treatment steps to prepare the sample before loading onto the separation media. In addition, embodiments of the spin filter assembly that include pulverizing agents, like glass beads, permit the disruption and or lysis of cells or tissues in the same device, eliminating additional time-consuming steps to prepare the sample for separation.

One embodiment of the present invention entails a method of separating a desired substance from other substances in a sample, including the steps of: a) providing a sample comprising a solution or suspension containing the desired substance; b) loading the sample onto the spin column assembly that contains an HGR-filter; c) placing the spin column assembly in a suitable collection vessel; d) applying sufficient force to the spin column assembly and collection vessel to drive fluids in the sample through the effluent port into the collection vessel; e) eluting the desired substance from the spin column assembly; and f) collecting the eluted substance in the collection vessel. In a preferred embodiment the desired substance is a biological molecule of interest, such as DNA, RNA, protein or glycoprotein. In another embodiment, the sample comprises disrupted cells or tissues suspended in lysis buffer. In some embodiments, sufficient force is applied to the spin column assembly and collection vessel by gravitation, pressure, vacuum or centrifugation. In a preferred embodiment, sufficient force is applied to the spin column assembly and collection vessel by centrifugation in a fixed angle rotor.

Another embodiment of the present invention entails a method of separating a biological molecule of interest from other substances in a sample, which includes the steps of: a) providing a sample comprising a solution or suspension containing the biological molecule of interest; b) obtaining a spin column assembly that includes a grinding or pulverizing agent; c) mixing the sample with the grinding or pulverizing agent in the spin column assembly; d) placing the spin column assembly in a suitable collection vessel; e) applying sufficient force to the spin column assembly and collection vessel to drive fluids in the sample through the effluent port into the collection vessel; e) eluting the biomolecule of interest from the spin column assembly; and f) collecting the eluted biomolecule of interest in the collection vessel. In one embodiment of the method, the mixing step includes mechanical agitation of the spin column assembly before or after placing the spin column assembly in a suitable collection vessel.

The disruption of the sample can be accomplished by its loading into the upper space in the column in the presence of suitable buffer or extraction fluid. For example, a suitable buffer or extraction fluid can include detergents such as 0.1% sodium dodecyl sulphate or TRITON® X100, ZONAL® fluoro-surfactants or similar; suitable buffering agents, such as Tris or MOPS or phosphate buffered saline; a pH adjustment agent providing a suitable pH from 0-14, such as 10-500 mM NaOH; or, in some instances, strongly chaotropic agents, such as saturated or six molar guinidinium thiocyanate for disruption of cells such as plant matter, tissue or bacterial cultures, biopsy specimens or whole tissues, which may or may not have been preserved with agents such as formalin. The selection of such lysis agents are known according to purpose by those skilled in the art.

The lysis is accomplished by adding a closure to the column top to prevent the exit of materials from the column and the mechanical agitation of the column with sufficient force as to mix the sample and the lysing agent and beads with sufficient force to disrupt the sample releasing its constituent components to the surrounding media, thereby creating an essentially homogeneous mixed suspension of sample and media and beads. The mechanical agitation may be accomplished by vortexing, rocking, shaking or sonication or combinations of these, such means being well known to practitioners of the art. The lysed sample constituents are obtained by placing the HGR-device into a suitable receiver support device after removing the end cap or closure from the exit port of the device such as a test tube or other suitable collection device. The assembled HGR-device and collection device is inserted into the centrifuge rotor suitable to accommodate the dimensions of the assembled device and is centrifuged at speed suitable to force the fluids through the column to exit the column and enter the receiving device.

The separation media in the HGR-device will determine which components of the lysate will be recovered from the process, for example if gel permeation separation media is used then usually small molecules will be retained by the HGR-device and the larger higher molecular weight contents which are soluble will be collected in the effluent discharged into the collection device.

Affinity chromatography is frequently used to selectively isolate unique substances from very complex mixtures such as expressed or cloned proteins from cells in which they may be expressed and this practice and methods for purification are well known by practitioners in the art. By inclusion of an appropriate or suitable affinity matrix as the separation media or in conjunction with other media in the present spin-columns described in the present application particular substances can be selected from other components of the mixture in which these substances may be found. For example the separation media may be comprised of protein A coated beads and the desired substance being IgG capable of being bound by the immobilized protein A within the described spin-column device set forth in this application. Application of serum containing the immunoglobulin to the device and its subsequent processing through the device will result in the applied IgG being retained by the Protein A affinity matrix in the column. Additional washes under conditions which will not release the bound IgG but remove residual serum components followed by application of buffer to release the bound IgG affords a simple method for the isolation of enriched IgG fractions from sera. Similarly as is well known in the art proteins can be selectively expressed with various tags or reporter groups to facilitate their purification. For example a protein coding sequence including a hexa-histidine tag motif can be cloned and expressed in cells. The expressed hexa-histidine tagged protein can the be captured by the described spin-column device containing hexa-histidine metal affinity resin beads and interfering or unbound materials washed away and the desired hexa-histidine tagged protein can then be eluted and collected in a highly enriched form. Likewise glycosylated proteins or carbohydrates or polysaccharides can similarly be obtained using affinity devices as described herein.

Kits

In one embodiment of the present invention, there is provided a kit containing a spin column assembly and one or reagents for use in the isolation of a desired substance, such as lysis buffer, wash buffer, elution buffer or stock solutions for preparing such buffers.

In another embodiment there is provided a kit comprising: a) one or more than one spin column device having an inner diameter and an inner radius; and b) one or more than one monolithic HGR filter assembly, the filter assembly having a diameter about equal to the inner diameter of the spin-column device and of a height greater than the inner radius of the spin-column device.

In addition to the various embodiments described above, the examples below are illustrative of the utility of the improvements to spin-columns achieved by the HGR-devices and HGR-filters subject of the present disclosure compared to those presently in general use.

EXAMPLE 1

Preparation of Various Embodiments of the Spin-Columns of this Disclosure

Empty spin-columns were obtained from Axygen (Union City, Calif.), e.g., AXYSPIN™ Mini spin-columns, or from Pierce Chemical Company (Rockford, Ill.), e.g., both unfilled or filled ZEBA™ 800 µl spin-columns.

In one embodiment, HGR-devices were prepared according to the foregoing disclosure as follows. Eight spin-columns, AXYSPIN™ Mini were obtained from Axygen (Union City, Calif.) and were packed using 666 µl of SEPHADEX® G-50 (~80% solids by volume in water with 0.1% sodium azide as preservative), which had been swollen overnight in water. The SEPHADEX® suspension was allowed to settle in each of the spin-columns for ~1 hour and then an HGR-filter comprised of 0.5 cm of a Rayo cellulose acetate cigarette filter (Uptown's Smoke Shop; Nashville, Tenn.) was placed in contact with the upper surface of the SEPHADEX® layer in each column. The filter absorbed the liquid above the SEPHADEX® and acted as an absorption and/or diffusion barrier to limit infiltration of liquids subsequently added to the spin-column prior to centrifugation. This embodiment is useful, for example, for the isolation of plasmid DNA from cell cultures and is represented in FIG. 1.

In another embodiment, HGR-devices were prepared according to the foregoing disclosure as follows. Spin-columns, AXYSPIN™ Mini columns were obtained from Axygen Biosciences (Union City, Calif.) and were packed using 400 µl of SEPHADEX® G-50 (~80% solids by volume in water with 0.1% sodium azide as preservative), which had been swollen overnight in water. The SEPHADEX® suspension was allowed to settle in each of the spin-columns for ~1 hour and then an HGR-filter comprised of 0.5 cm of a Rayo cellulose acetate cigarette filter (Uptown's Smoke Shop; Nashville, Tenn.) was placed in contact with the upper surface of the SEPHADEX® layer in each column. The filter absorbed the liquid above the SEPHADEX® and acted as an absorption and/or diffusion barrier to limit infiltration of liquids subsequently added to the spin-column. Next, 0.5 grams of 0.5 mm zirconia/silica beads (BioSpec Products; Bartlesville, Okla.) were added to the top of the HGR-filter in each spin-column to act as a mechanical lysis aid.

In another embodiment, HGR-devices were prepared according to the foregoing disclosure as follows. Spin-columns, AXYSPIN™ Mini columns were obtained from Axygen Biosciences (Union City, Calif.) and then an HGR-filter comprised of 2.0 cm of a Rayo cellulose acetate cigarette filter (Uptown's Smoke Shop; Nashville, Tenn.) was placed in contact with the upper surface of the lower frit in each column and appears in FIG. 3.

Similar columns of various configurations illustrated in FIGS. 1-3 were prepared from both filled and unfilled 800 µl capacity ZEBA™ columns (Pierce Chemical Company) with equal success.

EXAMPLE 2

Isolation of Ribosomal RNA from Microbial Cultures.

*Escherichia coli* strain ATCC 8739 (American Type Culture Collection; Manassas, Va.) and *Staphylococcus epidermidis* strain ATCC12228, (American Type Culture Collection) were each grown to confluence (approximately 48 hours) in 100 mls of TERRIFIC™ broth (Invitrogen, Carlsbad, Calif.). HGR-devices were prepared according to the foregoing disclosure as follows. Spin-columns were obtained from Axygen (Union City, Calif.) and were packed using 400 µl SEPHADEX® G-50 (~80% solids by volume in water with 0.1% sodium azide as preservative) which had been swollen overnight in water. The SEPHADEX® suspension was allowed to settle in each of the spin-columns for ~1 hour and then an HGR-filter comprised of a 0.5 cm of a Rayo cellulose acetate cigarette filter (Uptown's Smoke Shop; Nashville, Tenn.) was placed in contact with the upper surface of the SEPHADEX® layer in each column. The filter absorbed the liquid above the SEPHADEX® and acts as an absorption and/or diffusion barrier to limit infiltration of liquids subsequently added to the spin-column. Next, 0.5 grams of 0.5 mm zirconia/silica beads (BioSpec Products; Bartlesville, Okla.) was added to the top of the filter in each spin-column to act as a mechanical lysis aid.

Cell pellets were obtained from both overnight cultures above in duplicate by pipetting 2 mls of the appropriate culture to a 2 ml centrifuge tube and centrifuging at 2000×g for 3 minutes. The supernatant media was discarded and each of the cell pellets was resuspended in 500 µL of lysis buffer comprised of 100 mM MOPS (Sigma Aldrich, Saint Louis, Mo.), 10 mM EDTA (EMD Chemicals; VWR; West Chester, Pa.) 1% SDS (EMD Chemicals; VWR), 5 mM DTT (Amresco), 0.5% Antifoam A (Sigma Aldrich), 0.5% Antifoam Y (Sigma Aldrich), 50 µM aurinetricarboxylic acid (Sigma Aldrich) at a pH of ~7.0-7.2. The cell suspensions in lysis buffer were then transferred to the upper reservoir region of the HGR-devices described above in this example and were each capped with the cap provided with the spin-columns leaving the effluent closure at the tip of the spin-columns intact. These loaded HGR-devices were then placed in a Pulsing Vortex Mixer (ThermoFisher Scientific; Waltham, Mass.) and were processed using the "Pulse" setting of 3000 for 10 minutes. The caps were then removed and 50 μl of 400 mM potassium acetate pH 5.2 buffer was added to each of the vortexed HGR-devices and the caps were reapplied and then the HGR-devices were briefly vortexed to mix and were placed at ambient temperature (~23° C.) to incubate for three minutes. The effluent closure was broken from the tip of each HGR-device and then the devices were each inserted into 75 mm polycarbonate collection tubes which were then loaded into a fixed angle rotor of an ALLEGRA™ centrifuge equipped with a C1015 fixed angle rotor (Beckman Coulter; Fullerton, Calif.) and were centrifuged at 1500×g for two minutes. It was observed that all of the liquid in the columns had not been transferred to the collection tubes. Consequently, the spin-columns and the collection tube assemblies were centrifuged for an additional two minutes at 1500×g then an additional centrifugation at 3000×g for two minutes was performed at which time all of the visible liquid in the spin-columns was observed to pass into the collection tubes with recovery of approximately 500 μl each for the S. epidermidis duplicates and 700 μl for the E. coli sample duplicates. The spun columns were then transferred to a fresh collection tube and 100 μl of 10 mM sodium citrate pH ~6.8 was added to each spin-column and then centrifuged at 3000×g for five minutes resulting in recovery of essentially the entire 100 μl buffer volume applied to each column. Gel electrophoresis for the presence of ribosomal RNA was performed using 4 μl of each of the column effluents using a Lonza RNA flash gel system (Lonza; Rockland, Me.) and following the manufacturer's recommendations. The electrophoresis clearly indicated the presence of ribosomal RNAs from each sample and also in the additional column wash. The bands observed were consistent with 16S and 23S ribosomal RNAs from prokaryotic bacterial cells and also co-migrated with control known ribosomal RNAs. These results indicate that cell lysis and isolation of ribosomal RNA can be conducted in a single tube spin-column device prepared according to the present disclosure. An image of the gel was obtained using a Kodak Gel Logic Imaging system (Kodak; Rochester, N.Y.). The resulting image of the gel and its annotation appears as FIG. 6, where the arrow indicates the region for ribosomal RNA and the lanes contained the following samples:

| Lane | Sample |
|---|---|
| 1 | 4 ul of E. coli tube 1 (first filter spin) |
| 2 | 4 ul of E. coli tube 1 (first filter spin) |
| 3 | 4 ul of E. coli tube 2 (100 ul 2nd spin) |
| 4 | 4 ul of E. coli tube 2 (100 ul 2nd spin) |
| 5 | 4 ul of S. epidermidis tube 1 (first filter spin) |
| 6 | 4 ul of S. epidermidis tube 1 (first filter spin) |
| 7 | 4 ul of S. epidermidis tube 2 (100 ul 2nd spin) |
| 8 | 4 ul of S. epidermidis tube 2 (100 ul 2nd spin) |
| 9 | Control RNA |

EXAMPLE 3

Isolation of a Plasmid from Cell Culture

An E. Coli strain DH5α carrying a pGEM 7Zf-plasmid of ~3 Kb nucleotides (actual 2998 bp) in length (Promega; Madison, Wis.) was grown in 100 mls CIRCLEGROW® media (MP Biomedicals, LLC.; Solon, Ohio) supplemented with 100 μg/ml ampicillin (Sigma Aldrich) to confluence in a model C25 Incubator Shaker (New Brunswick Scientific; Edison, N.J.) at ~37° C. Duplicate 1 ml aliquots of the culture were transferred to 2 ml centrifuge tubes (Sarstedt; Newton, N.C.) and bacteria were pelleted by centrifugation at 2000×g for 3 minutes in an IEC MicroMax RF centrifuge (IEC; Thermo Scientific; Waltham, Mass.). The media was discarded from the cell pellets and the pellets were resuspended in 200 μL S1 aqueous buffer comprised of 50 mM Tris-HCl, 10 mM EDTA, 100 μlg/ml RNase A (Macherey-Nagel; Bethlehem, Pa) and then 200 μL of S2 aqueous buffer comprised of 200 mM NaOH, 1%SDS (Macherey-Nagel) was then added to the cell suspension. The mixture was incubated at ambient temperature (~23° C.) for three minutes. The HGR-devices were prepared consisting of an Axygen Biosciences AXYSPIN™ with 400 μl of 80% solids suspension of SEPHADEX® G-50 (Sigma Aldrich) swollen in water with 0.1% sodium azide as preservative with an HGR-filter comprised of a 0.5 cm Rayo cellulose acetate filter (Uptown's Smoke Shop; Nashville, Tenn.) seated atop the G-50 gel to which 200 μl of S3 aqueous buffer comprised of 2.8M potassium acetate pH 5.1 (Macherey-Nagel) was added. The lysed solution of bacteria was applied to the treated spin-column and briefly mixed to allow precipitate to form. The spin column was then placed in a 75 mm polystyrene tube (Sarstedt) and the assembly was centrifuged in an ALLEGRA™ 21 equipped with a C1015 rotor (Beckman Coulter, Fullerton, Calif.) at 1000×g for five minutes. The HGR-devices were discarded and the collected filtrates estimated to be ~500 μl each were analyzed for their A260 and A280 values to determine DNA concentration and estimate their purity using a Nanodrop® ND-1000 instrument (Thermo Scientific). The values obtained were ~143 ng/μl for the first duplicate and ~256 ng/μl for the second replicate with the respective A260/A280 ratios of 2.11 and 2.05 indicating excellent plasmid yields and purity. To demonstrate the suitability of the isolated plasmids for downstream applications such as sequencing, cloning, PCR and the like, the recovered plasmid solutions were transferred to a 2 ml Sarstedt centrifuge tube and were treated with 1 ml of isopropanol. The DNA was observed to precipitate almost immediately on this addition. The DNA was pelleted following 5 minutes of incubation at room temperature by centrifugation in a MicroMax RF centrifuge with an 851 rotor (IEC; Thermo Scientific) at 12000×g for 5 minutes. The isopropanol phase was decanted and the pellets were each washed with 500 μl of 95% ethanol and then centrifuged for 1 minute at 12,000×g in the MicroMax centrifuge. The ethanol was removed from the pellets and the pellets were dried under vacuum for five minutes in a SPEED-VAC® (Savant; Thermo Scientific). The pellets were each resuspended in 100 μl 0.1×TE, 2% acetonitrile buffer pH 8.0. An aliquot of 20 μl of each of the plasmid solutions was then digested for one hour at 37° C. with 10 units of the restriction endonuclease Bam HI with buffering provided by the addition of 2.2 μl SureCut buffer B (Roche Molecular; Indianapolis, Ind.). This was followed by electrophoretic analysis using 5 μl of both replicates of the isolated undigested plasmids and the Bam HI digested plasmids which were applied and electrophoresed using an eight well pre-cast 1% agarose gel (Lonza; Rockland, Me.) compared to a BIOMARKER® 10 KB molecular sizing standard (BioVentures, Inc; Murfreesboro, Tenn.) with the ethidium bromide gel imaged using a Kodak Gel logic Imaging System (Kodak; Rochester, N.Y.). The resulting image appears below as FIG. 7, where the arrow indicated the 3 KB linear DNA region and the lanes contained the following samples:

| Lane | Sample |
| --- | --- |
| 1 | Empty |
| 2 | 5 uL of 3 kb plasmid isolated with single tube |
| 3 | 5 uL of Bam HI digested plasmid |
| 4 | 5 uL of 3 kb plasmid isolated with single tube |
| 5 | 5 uL of Bam HI digested plasmid |
| 6 | 5 ul 10 KB marker |
| 7 | Empty |
| 8 | Empty |

The duplicate plasmid isolations clearly indicate essentially 100% cutting by Bam HI to yield a ~3Kb linear DNA based on the single Bam HI restriction site in the plasmids. Consequently, the isolated plasmids are useful for many downstream applications.

EXAMPLE 4

Example Comparing RNA Isolation Methods

Comparison of time and yields of application spin column device with two commercial RNA isolation methods. *E. coli* was grown overnight to confluence in 25 milliliters of sterile Letheen Broth at 31° C. and 200 RPM in a shaker incubator. A suitable aliquot of the culture was processed by the method of Example 2 for the present spin filter device and also using a MoBio Ultra Clean Microbial RNA isolation kit following the manufacturer's protocol as well as a Qiagen RNeasy minikit following the manufacturer's protocol except omitting the DNase treatment. All procedures yielded rRNA and total RNA suitable for downstream analysis by electrophoretic analysis of the RNA obtained from the bacterial culture. However, the spin column device as employed per Example 2 required very little hands on time, being on the order of five minutes and a total time to recover the RNA of less than twenty minutes, including the hands on time involved in transfers and handling. In contrast the two commercial kits required in excess of forty minutes to perform and an additional five or so minutes of handling and manipulation time, with both being completed in about a total of forty-five minutes. Consequently, the method and device of the present application can be completed in half the time of two frequently used commercial RNA isolation kits. When multiple samples were compared even greater savings of time and substantial reductions in manipulations and transfers were noted for the present spin filter device compared to the commercial kits above. The device and the process of Example 2 requires a maximum of five steps: (1) Pelleting the cells, (2) resuspending the cell pellet with lysis buffer, (3) loading the cells on the lysis spin-column assembly, (4) lysing the cells in the spin-column, (5) centrifugation of the spin-column and collecting the filtrate in a suitable collection device (tube). The MoBio protocol requires at least 16 discrete steps and the Qiagen protocol even omitting the DNase digestion step still requires 18 discrete steps. Similar preparations were made from cultures of additional organisms with equally good comparable results.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features.

The present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A spin column assembly, comprising:
   a) a spin column device, the spin column device comprising:
      1) a column, the column comprising an inner diameter and an upper opening,
      2) a lower end, the lower end comprising an effluent port, wherein the effluent port comprises an opening small enough to retain or impede the exit of solid or particulate matter from the spin column device, but large enough to allow passage of effluent liquids;
   b) a separation media suspension contained within the spin column device, the separation media suspension comprising an upper surface;
   c) a rigid porous filter placed within the spin column device above the separation media suspension and in close contact with the upper surface of the column separation media suspension, the porous filter comprising a filter diameter no greater than or equal to the inner diameter of the spin column and a filter height greater than half the inner column diameter;
   d) a volume control device for regulating the volume of fluid delivered to the upper surface and center of the spin column assembly, wherein the volume control device is placed within the upper opening of the spin column device and above the rigid porous filter, the volume control device comprising:
      i) an outer column;
      ii) a base attached below the outer column, the base comprising a hole, wherein the hole in the base impedes or prevents the flow of fluid due to surface tension effects under normal gravity, but permits the flow of fluid through the hole under higher gravitational or other forces;
   e) a hollow inner cylinder attached to the base and situated within the outer cylindrical column, the inner cylinder comprising a height and inner diameter;
   f) a first cavity within the hollow inner cylinder and above the base comprising a fixed volume, wherein the height and inner diameter of the inner cylinder determines the fixed volume; and
   g) a second cavity outside the inner cylinder, but within the outer column and above the base,
   wherein any excess of fluid delivered to the first cavity will overflow and be retained in the second cavity without being delivered to the upper surface of the spin column assembly and only the fluid in the first cavity will pass through the lower opening onto the receiving spin column assembly.

2. The spin column assembly of claim 1, wherein the filter height of the rigid porous filter is equal to the inner column diameter.

3. The spin column assembly of claim 1, wherein the rigid porous filter is inflexible enough to maintain its shape upon application of centrifugal force of at least 1,000 ×g.

4. The spin column assembly of claim 1, wherein in the rigid porous filter comprises a fiber selected from the group consisting of cellulose, cellulose acetate, nitrocellulose, polyethylene, nylon and polytetrafluoroethylene (PTFE).

5. The spin column assembly of claim 1, wherein the rigid porous filter comprises a sintered material selected from the group consisting of plastic, ceramic and metal.

6. The spin column assembly of claim 1, wherein the separation media suspension is selected from the group consisting of cross-linked dextrans, polyacrylamides, cellulose particles, ion exchange resins, silica particles, silica gels, and affinity chromatography media.

7. The spin column assembly of claim 1, wherein the spin column device comprises plastic, glass or treated paper.

8. The spin column assembly of claim 1, wherein the effluent port comprises a screen.

9. The spin column assembly of claim 1, further comprising a media support seated above the lower end and below the separation media suspension.

10. The spin column assembly of claim 9, wherein the media support comprises a polyethylene frit, filter paper or membrane.

11. The spin column assembly of claim 1, further comprising a column effluent collection vessel.

12. The spin column assembly of claim 1, further comprising a grinding agent or pulverizing agent placed above the rigid porous filter, wherein the grinding agent or pulverizing agent comprises a plurality of beads made of ceramics, glass or metal or combinations of the preceding beads.

13. The spin column assembly of claim 12, further comprising a protective frit situated between the rigid porous filter and the grinding agent or pulverizing agent.

14. The spin column assembly of claim 12, wherein the grinding agent or pulverizing agent comprises zirconia/silica beads.

15. The spin column assembly of claim 1, further comprising a cap covering the upper opening of the spin column device.

16. The spin column assembly of claim 1, further comprising a closure plugging the effluent port.

17. The spin column assembly of claim 1, wherein the volume control device comprises a rigid, inert material impermeable to liquids.

18. The spin column assembly of claim 1, wherein the volume control device comprises paper impregnated with polymer, metal, glass or plastic.

19. The spin column assembly of claim 1, wherein the volume control device comprises injection molded plastic.

20. The spin column assembly of claim 1, the volume control device comprising an internal volume, wherein the internal column volume is between 200 µl to 20 ml.

21. A method of separating a biological molecule of interest from other substances in a sample, comprising:
  a) providing a sample comprising a solution or suspension comprising the biological molecule of interest;
  b) providing the spin column assembly of claim 12;
  c) mixing the sample with the grinding or pulverizing agent in the spin column assembly;
  d) placing the spin column assembly in a suitable collection vessel;
  e) applying sufficient force to the spin column assembly and collection vessel to drive fluids in the sample through the effluent port into the collection vessel;
  f) eluting the biomolecule of interest from the spin column assembly; and
  g) collecting the eluted biomolecule of interest in the collection vessel.

22. The method of claim 21, wherein the mixing step (c) comprises mechanical agitation of the spin column assembly before or after placing the spin column assembly in a suitable collection vessel.

23. A kit comprising:
  a) a spin filter assembly according to claim 1; and
  b) one or more than one reagent for use in an isolation or purification procedure selected from the group consisting of lysis buffer, wash buffer, elution buffer and stock solutions for preparing the preceding buffers.

* * * * *